(12) United States Patent
James et al.

(10) Patent No.: US 7,223,865 B2
(45) Date of Patent: May 29, 2007

(54) CHROMOGENIC COMPOUNDS, AND USE THEREOF AS ENZYME SUBSTRATES

(75) Inventors: Arthur James, Rothbury (GB); Annette Rigby, Haltwhistle (GB)

(73) Assignee: Biomerieux, Marcy l'Etoile (FR)

( * ) Notice: Subject to any disclaimer, the term of this patent is extended or adjusted under 35 U.S.C. 154(b) by 0 days.

(21) Appl. No.: 10/541,490

(22) PCT Filed: Jan. 26, 2004

(86) PCT No.: PCT/FR2004/050031
§ 371 (c)(1),
(2), (4) Date: Jul. 7, 2005

(87) PCT Pub. No.: WO2004/069804
PCT Pub. Date: Aug. 19, 2004

(65) Prior Publication Data
US 2006/0035306 A1 Feb. 16, 2006

(30) Foreign Application Priority Data
Jan. 29, 2003 (FR) .................................. 03 00953

(51) Int. Cl.
*C07D 219/00* (2006.01)
*C12Q 1/37* (2006.01)
(52) U.S. Cl. ........................................ 546/102; 435/24
(58) Field of Classification Search .................... None
See application file for complete search history.

(56) References Cited

U.S. PATENT DOCUMENTS 4,457,866 A   7/1984   Karges et al.

FOREIGN PATENT DOCUMENTS

| EP | 0 270 946 A2 | 6/1988 |
|----|--------------|--------|
| EP | 0 656 421 A1 | 6/1995 |
| FR | 2 659 982 A1 | 9/1991 |
| WO | WO 98/04735 A1 | 2/1998 |
| WO | WO 99/09207 A1 | 2/1999 |
| WO | WO 99/38995 A1 | 8/1999 |
| WO | WO 01/09372 A1 | 2/2001 |

OTHER PUBLICATIONS

S. Rapposch et al.; "Influence of Fluorescence of Bacteria Stained with Acridine Orange on the Enumeration of Microorganisms in Raw Milk"; *J. Dairy Sci.*; vol. 83, No. 12; 2000; pp. 2753-5758.
A. Giorgio et al.; "Detection of Microorganisms in Clinical Specimens Using Slides Prestained with Acridine Orange (AOS)"; *Microbiologica*; vol. 12, No. 1; 1989; pp. 97-100.
Nadine Costes et al.; "Synthesis and Cytotoxic and Antitumor Activity of Benzo[b ]pyrano[3,2- i h l ]acridin-7-one Analogues of Acronycine"; *J. Med. Chem.*; vol. 43, No. 12; 2000; pp. 2395-2402.
O. Okwumabua et al.; "Evaluation of chemiluminescent DNA probe assay for the rapid confirmation of *Listeria monocytogenes*"; *Res. Microbiol.*; vol. 143, No. 2; 1992; pp. 183-189.
Thomas Schelhorn et al.; "Review, Reinvestigation of the Binding of Proflavine to DNA. Is Intercalation the Dominant Binding Effect?"; *Cellular and Molecular Biology*; vol. 38, No. 4; 1992; pp. 345-365.
Adrien Albert; *The Acridines: Their Preparation, Physical, Chemical, and Biological Properties and Uses*; 1966; second edition; pp. 29-55.
A. Campbell et al.; "5-Alkylacridines. Part I. Synthesis of 5-Methylacridine and Certain Substituted Analogues"; *J. Chem. Soc.*; 1958; pp. 1145-1149.

*Primary Examiner*—Jon Weber
*Assistant Examiner*—Paul Martin
(74) *Attorney, Agent, or Firm*—Oliff & Berridge, PLC

(57) ABSTRACT

The present invention relates to novel chromogenic substrates which are used to detect aminopeptidase activity in microorganisms or to determine whether at least one bacterium belongs to the Gram-positive group or to the Gram-negative group according to the color thereof. The invention also relates to culture media containing such substrates, to the use of the substrates or media for the detection of aminopeptidase activities and/or the differentiation of Gram-positive bacteria from Gram-negative bacteria and to methods of use.

The aforementioned novel substrates have the formula below:

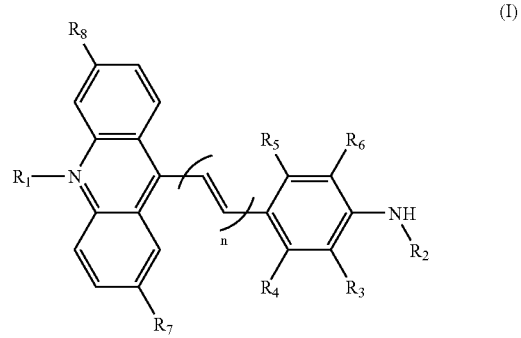

(I)

in which:
$R_1$ is nothing or an alkyl, allyl or aryl group,
$R_2$ consists of at least one amino acid, preferably alanine,
$R_3$, $R_4$, $R_5$ and $R_6$ consist, independently of one another, of H— or —O-alkyl, preferably —O—$CH_3$,
$R_7$ consists of H, O—$CH_3$, alkyl or halogen,
$R_8$ consists of H or Cl, and
n is an integer corresponding to 0 or 1.

The invention is particularly suitable for use in the field of diagnostics.

17 Claims, No Drawings

CHROMOGENIC COMPOUNDS, AND USE THEREOF AS ENZYME SUBSTRATES

The present invention relates to novel chromogenic enzyme substrates for detecting aminopeptidase activity. The substrates can be used in applications comprising an enzymatic hydrolysis step that produces a physicochemical signal, in particular in microbiology, biochemistry, immunology, molecular biology, histology, etc. The invention also relates to culture media containing such substrates, to the use of the substrates or of the media for detecting aminopeptidase activities and/or differentiating Gram-positive bacteria from Gram-negative bacteria and to methods of use.

Compared to existing substrates, most of which are fluorogenic, these novel substrates can be used in particular in gelled media for detecting microorganisms since they produce a coloration that does not diffuse in the reaction medium and is therefore concentrated in the colonies.

Chromogenic enzyme substrates for detecting aminopeptidase activity that do not diffuse are described and already known from the state of the art. Thus, such substrates are covered by patent applications WO-A-98/04735 and WO-A-99/38995 filed by the applicant. Nevertheless, these substrates have various drawbacks: they are difficult to synthesize, the purity is low and the yields are low. In addition, for use in culture media, it is necessary to define a very precise medium composition in order to observe a color. None of the other substrates currently described can be used in solid media for detecting microorganisms in mixed cultures.

In addition, acridine-based molecules are known. They are used for:

their dye properties, see, for example, S. Rapposch et al., J. Dairy Sci. December 2000; 83 (12) : 2753–2758, or else, for example, A. Giorgio et al., Microbiologica January 1989; 12(1) : 97–100, their chemotherapeutic properties, for example N. Costes et al., J. Med. Chem. Jun. 15, 2000; 43(12): 2395–2402, or performing intercalations in DNA, for example O. Okwumabua et al., Res. Microbiol. February 1992; 143 (2): 183–189, or else, for example, T. Schelhorn et al., Cell. Mol. Biol. July 1992; 38(4) : 345–365.

Patent EP-B-0.270.946 proposes chromogenic enzyme substrates based on acridinone, which is a derivative of acridine. The radical, which can be cleaved by an enzyme, is present at position 7 of the acridine group. Its structure makes it possible to visualize only the following enzyme activities: esterases and glycosidases.

In accordance with the present invention, novel chromogenic enzyme substrates for detecting aminopeptidase activity in microorganisms or for determining whether at least one bacterium belongs to the Gram-positive group or the Gram-negative group according to the color thereof are proposed. The invention also relates to culture media containing such substrates, to the use of the substrates or of the media for detecting aminopeptidase activities and/or differentiating Gram-positive bacteria in relation to Gram-negative bacteria, and to methods of use.

To this effect, the present invention relates to chromogenic enzyme substrates for detecting aminopeptidase activity in microorganisms or for determining whether at least one bacterium belongs to the Gram-positive group or the Gram-negative group according to the color thereof. They have formula (I) below:

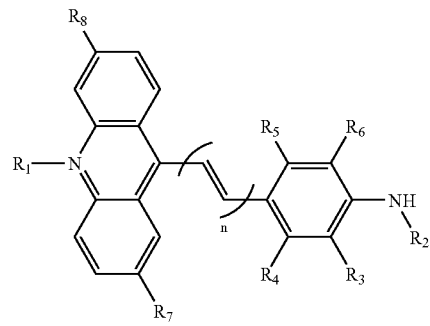

(I)

in which:
R$_1$ is nothing or an alkyl, allyl or aryl group,
R$_2$ consists of at least one amino acid, preferably alanine,
R$_3$, R$_4$, R$_5$ and R$_6$ consist, independently of one another, of H— or —O-alkyl, preferably —O—CH$_3$,
R$_7$ consists of H, O—CH$_3$, alkyl or halogen,
R$_8$ consists of H or Cl, and
n is an integer corresponding to 0 or 1.

According to the invention, the term "aryl" in particular is intended to mean a C$_6$–C$_{10}$ aromatic ring, in particular phenyl, benzyl, 1-naphthyl or 2-naphthyl.

The term "alkyl" is intended to mean a C$_1$–C$_6$ alkyl, i.e. a straight or branched alkyl having from 1 to 6 carbon atoms. By way of example, mention may be made of methyl, ethyl, propyl, isopropyl, butyl, t-butyl, pentyl, isopentyl and hexyl.

The term "halogen atom" is intended to mean chlorine, bromine, iodine and fluorine.

The amino acids used in the invention are any amino acid known to those skilled in the art.

The expression "at least one amino acid" is intended to mean one or more amino acids.

According to one embodiment of the invention, R$_2$ represents an amino acid or a peptide having at most 10 amino acids in which the amino acids are identical or different. Preferably, for reasons of substrate cost, A represents an amino acid or a peptide having at most 4 amino acids in which the amino acids are identical or different, preferably identical.

The amino acid(s) R$_2$ can be coupled to a blocking agent, which constitutes another embodiment of the invention.

These blocking agents comprise any blocking agent known to those skilled in the art that is capable of protecting amines. By way of example, mention may be made of t-butoxycarbonyl (N-tBOC), 9-fluorenyloxy-carbonyl, a solubilizing agent such as succinyl, or else a non-metabolizable, i.e. non-natural, amino acid such as pipecolic acid.

According to one embodiment, the substrate has formula (Ia) below:

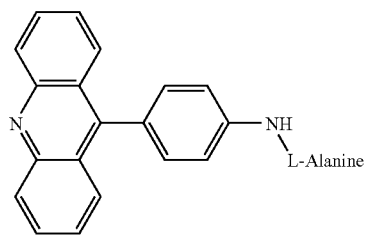

(Ia)

or it has formula (Ib) below:

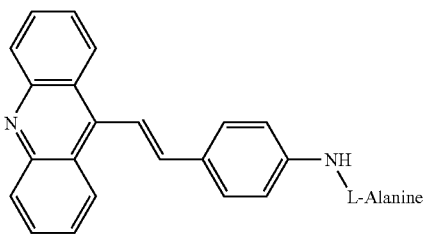

According to another embodiment, the substrate corresponds to formula (I) above in which $R_1$ is a methyl or allyl group.

According to yet another embodiment, the substrate corresponds to formula (I) above in which $R_1$ is an alkyl, preferably methyl, group or an allyl group, $R_2$ is at least one amino acid, optionally blocked with a blocking agent, preferably at least one alanine, $R_3$, $R_4$, $R_5$, $R_6$, $R_7$ and $R_8$ are H, and n is 0 or 1.

According to yet another embodiment, the substrate has formula (Ic) below:

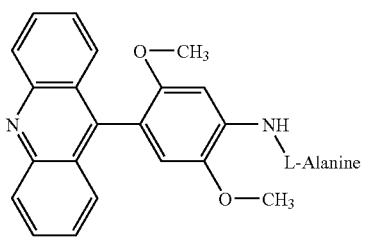

or it has formula (Id) below:

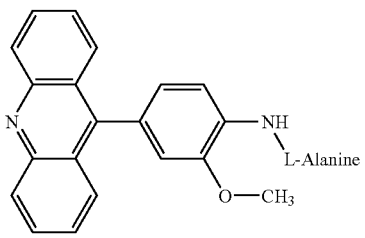

The compounds of the invention can be prepared according to the value of n, as follows:

(1) When n=0, appropriate acridine hydrochloride ($R_8$ is H or Cl) is reacted with appropriate aniline ($R_3$, $R_4$, $R_5$ and $R_6$ being as defined above) and sulfur, so as to obtain the appropriate 9-(4-aminophenyl)acridine. The latter is then reacted with at least one amino acid coupled to a blocking agent and the compound obtained is optionally deprotected so as to separate the blocking agent from the compound of the invention. When it is desired to obtain a compound for which the nitrogen in the 10-position is quaternized, the compound obtained is reacted with an $XR_1$ in which X is a halogen and $R_1$ is as defined above, and (2) When n=1, 9-methylacridine, prepared according to the method of Campbell et al. (1958, above), or 9-chloroacridine, prepared according to the method of Lehmstedt and Schrader (Albert, 1966, above), is reacted with appropriate nitrobenzaldehyde ($R_3$, $R_4$, $R_5$ and $R_6$ being as defined above) and zinc chloride so as to prepare appropriate 9-(4-nitrostyryl)acridine. The nitro group is then reduced either with tin(II) chloride in a mixture of ethyl acetate and ethanol, or with sodium borohydrate and copper acetylacetonate, so as to obtain 9-(4-aminostyryl)acridine. The latter is then reacted with at least one amino acid coupled to a blocking agent and the compound obtained is optionally deprotected so as to separate the blocking agent from the compound of the invention. When it is desired to obtain a compound for which the nitrogen in the 10-position is quaternized, the compound obtained is reacted with $XR_1$ in which X is a halogen and $R_1$ is as defined above.

The invention also relates to a culture medium using at least one chromogenic enzyme substrate as defined above, alone or in combination with at least one other enzyme substrate specific for an enzyme activity that is other than an activity of that detected by the substrate according to the invention.

As a result, when microorganisms expressing peptidase activity are seeded into a reaction medium containing the compounds of the invention, a coloration occurs that does not diffuse into the reaction medium, and is therefore concentrated in the colonies.

The expression "reaction medium according to the invention" is intended to mean a medium that allows the development of at least one enzyme activity of at least one microorganism.

This reaction medium may either be used only as a visualizing medium, or as a culture medium and visualizing medium. In the first case, the culturing of the microorganisms is carried out before seeding and, in the second case, the reaction medium also constitutes the culture medium.

The reaction medium may be solid, semi-solid or liquid. The term "solid medium" is intended to mean, for example, a gelled medium.

Preferably, this medium consists of a gelled medium.

Agar is the conventional gelling agent in microbiology for culturing microorganisms, but it is possible to use gelatine or agarose. A certain number of preparations are commercially available, for instance Columbia agar, Trypcase-soy agar, MacConkey agar, Sabouraud agar or, more generally, those described in the Handbook of Microbiological Media (CRC Press).

The amount of agar in the reaction medium is from 2 to 40 g/l, and preferably from 9 to 25 g/l.

The enzyme substrates of the invention can be used within a broad pH range, in particular between pH 5.5 and 10.

The concentration of enzyme substrate of the invention in the reaction medium is between 0.025 and 1.0 g/l, and it is advantageously 0.3 g/l. Specifically, at this substrate concentration, a better color contrast is obtained.

The reaction medium can comprise at least one other substrate specific for an enzyme activity other than that detected by the substrate according to the invention. The enzymatic hydrolysis of the other substrate(s) generates a detectable signal that is different from the signal detected by the substrate of the invention, for instance different colored or fluorescent products, so as to allow the demonstration, such as the detection and/or the identification and/or the quantification, of one or more microorganisms.

As another specific substrate, use may be made of any other substrate conventionally used in the detection of microorganisms.

The concentration of the other specific enzyme substrate is generally between 0.01 and 2 g/l. Those skilled in the art will be able to readily determine such a concentration according to the substrate used.

The reaction medium can also comprise one or more elements in combination, such as amino acids, peptones, carbohydrates, nucleotides, minerals, vitamins, antibiotics, surfactants, buffers, phosphate salts, ammonium salts, sodium salts or metal salts. Examples of media are described in the applicant's patent applications EP 656 421 and WO 99/09207.

The enzyme substrates and reaction media of the invention are therefore useful in the diagnosis of microorganisms with peptidase activity.

Thus, the present invention also relates to the use of the chromogenic enzyme substrates as defined above, or of a culture medium also described above, for detecting at least one aminopeptidase activity in microorganisms.

A subject of the present invention is still the use of the chromogenic enzyme substrates as described above, or of a culture medium also described above, for separating bacteria with Gram-positive coloration from bacteria with Gram-negative coloration.

Finally, the invention relates to a method for detecting at least one aminopeptidase activity in microorganisms, this method consisting in:

providing a culture medium as defined above, seeding the medium with a biological sample to be tested, leaving it to incubate, and visualizing the presence of at least one aminopeptidase activity, alone or in combination with at least one other different enzyme activity.

The invention also relates to another method for differentiating bacteria in terms of whether they belong to microorganisms of the Gram-positive type or to microorganisms of the Gram-negative type, this method consisting in:

providing a culture medium as defined above, seeding the medium with a biological sample to be tested, leaving it to incubate, and visualizing the presence of at least one color synonymous with the presence of a microorganism or microorganisms of the Gram-negative type.

Whatever the method used, when the nitrogen in the 10-position of the acridine group is not quaternized, the presence of at least one aminopeptidase activity is visualized by adding acid, preferably hydrochloric acid, acetic acid or citric acid, to the culture. The term "quaternized" should be understood to mean that the nitrogen in the 10-position of the acridine group is tetravalent, i.e. it is linked via three conventional bonds with the phenyl ring and a supplementary bond with a radical, such that said nitrogen atom carries a positive charge and is therefore cationic. In this case, the molecule is in the form of a salt, for example a chloride, bromide or trifluoroacetate salt.

All the reactions, which will be described below in the examples, were monitored by thin layer chromatography (TLC) and the structures of the products were confirmed by mass spectrometry (MS) and nuclear magnetic resonance (NMR).

EXAMPLE 1

Visualization of the L-alanine-amino-peptidase Activity of Microorganisms on Gelled Medium Using Nonquaternized Substrates 1.1: Molecules Used:

A comparative study of two acridine-based substrates was carried out, these substrates being L-alanyl-9-(4-aminostyryl)acridine, hereinafter referred to as L-Ala-4-ASA, and L-alanyl-aminophenylacridine (nonquaternized substrates), hereinafter referred to as L-Ala-APA, having the respective formulae:

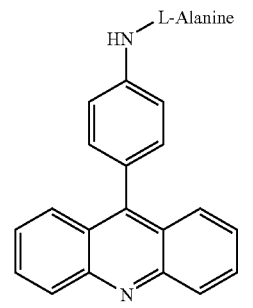

L-alanyl-aminophenylacridine

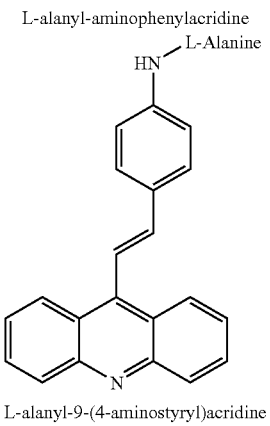

L-alanyl-9-(4-aminostyryl)acridine 1.2: Synthesis of Substrates:
  1.2.1: Synthesis of L-Ala-4-ASA:
  This synthesis is carried out in several steps.

Preparation of 9-chloroacridine

The preparation is carried out using the Lehmstedt and Schrader method, which was referenced by Albert in his book "The Acridines", Arnold, second edition, (1966), page 33.

Preparation of 9-methylacridine

The method of Campbell, Franklin, Morgan and Tivey (ref. *J. Chem. Soc.*, 1958, 1145) was used. The yields reached 90%.

Preparation of 9-(4-nitrostyryl)acridine by Melting

A mixture of 9-methylacridine (4.83 g, 25.0 mmol), 4-nitrobenzaldehyde (4.23 g, 31.25 mmol) and zinc chloride (5.06 g, 31.25 mmol) is heated at 130° C. for 3 hours with an oil bath. The solid recovered is heated in a solution of sodium metabisulfite in order to eliminate the excess aldehyde and the hot mixture is filtered. Precipitates obtained are dissolved in a minimum amount of tetrahydrofuran and water is added to the solution so as to obtain the product in the form of precipitates. These precipitates are recovered by filtration and dried. The product can be recrystallized from ethanol. The yield is 35%.

Preparation of 9-(4-aminostyryl)acridine

The 9-(4-nitrostyryl)acridine product (2.86 g, 10.0 mmol) is dissolved in ethyl acetate (250 ml) and then brought to reflux. A solution of tin(II) chloride dehydrate (9.0 g, 40 mmol) in hot ethanol (150 ml) is cooled and added to the solution of 9-(4-nitrostyryl)acridine. The mixture is reacted under reflux and with stirring for 5 hours. After cooling, the 9-(4-aminostyryl)acridine precipitates and is isolated by filtration under vacuum. The filtrate is dried by evaporation and taken up in water (500 ml) with stirring. The solution is basified (pH 13–14) with a sodium hydroxide solution. The 9-(4-aminostyryl)acridine fraction previously isolated, which contains a high proportion of tin salt, is also basified. The 9-(4-aminostyryl)acridine is separated by filtration, washed with water and dried. It is sufficiently pure for the following step.

Preparation of
t-Boc-alanyl-9-(4-aminostyryl)acridine

The t-Boc-alanine product (3.79 g, 20.0 mmol) is dissolved in a minimum amount of anhydrous tetrahydrofuran (THF) and the solution is cooled to –15° C. by means of a mixture of ethylene glycol/dry ice in a bath. N-methylmorpholine (NMM) (2.02 g, 20 mmol) is added dropwise to the mixture. Isobutyl chloroformate (IBCF) (2.53 g, 20.0 mmol) is then introduced dropwise into the reaction mixture. The temperature must be below –10+ C. After approximately 3 minutes, the 9-(4-aminostyryl)acridine (5.4 g, 20 mmol), which is dissolved in a minimum amount of anhydrous tetrahydrofuran (THF) and cooled to –15° C., is introduced. The reaction mixture is stirred and allowed to return to ambient temperature. The N-methyl-morpholine salt is eliminated by filtration with a funnel containing a filter plate. The mixture is evaporated down to a quarter of its original volume with a rotary evaporator. The filtrate is introduced dropwise into a mixture of water/ice in large amount, with stirring. Yellow precipitates, which are formed, are recovered by filtration, washed with water and dried. The product can be recrystallized from methanol. The yield is substantially 75%.

Other t-Boc-protected amino acid analogs were also used to form novel products. The amino acids are: proline, glycine, serine and β-alanine. The yields for these products are in the region of 60 to 80%, the best results generally being for the β-alanine analogs and the worst results generally being for the serine analogs.

1.2.2: Synthesis of L-Ala-APA:

The preparation of 9-(4-aminophenyl)acridine by reaction of molten sulfur can be carried out by means of two different methods.

Method A

The acridine hydrochloride (9.7 g, 45.0 mmol), the aniline (8.37 g, 90.0 mmol) and 10.0 g of sulfur are well mixed and heated at 130° C. for 4 hours under an efficient hood. The reaction medium in the round-bottomed flask is cooled to ambient temperature and dissolved in hot methanol so as to give a blood red-colored solution. The solution is cooled and the sulfur is eliminated by filtration. The filtrate is basified using a concentrated aqueous ammonia solution. Light yellow precipitates, that are formed, are filtered and then washed with cold methanol. The yield is 65%.

Method B

The acridine (8.06 g, 45.0 mmol), the aniline hydrochloride (11.61 g, 90 mmol) and 10.0 g of sulfur are well mixed and heated at 130° C. for 4 hours. The reaction medium is then treated as in method A above. A preparation is then realized on the basis of one and/or the other of the two methods above.

Preparation of
t-Boc-alanyl-9-(4-aminophenyl)acridine

The t-Boc-alanine product (3.79 g, 20.0 mmol) is dissolved in a minimum amount of anhydrous tetrahydrofuran (THF) and the solution is cooled to –15° C. by means of a mixture of ethylene glycol/dry ice in a bath. N-methylmorpholine (NMM) (2.02 g, 20 mmol) is added dropwise to the mixture. Isobutyl chloroformate (IBCF) (2.53 g, 20.0 mmol) is then introduced dropwise into the reaction mixture. The temperature must be below –10° C. After approximately 3 minutes, the 9-(4-aminophenyl)acridine (5.4 g, 20 mmol), which is dissolved in a minimum amount of anhydrous tetrahydrofuran (THF) and cooled to –15° C., is introduced. The reaction mixture is stirred and allowed to return to ambient temperature. The N-methyl-morpholine salt is eliminated by filtration with a funnel containing a filter plate. The mixture is evaporated down to a quarter of its original volume with a rotary evaporator. The filtrate is introduced dropwise into a mixture of water/ice in large amount, with stirring. Yellow precipitates, that are formed, are recovered by filtration, washed with water and dried. The product can be recrystallized from methanol. The yield is 75%.

Other t-Boc-protected amino acid analogs were also used to form novel products. The amino acids are: proline, glycine, serine and β-alanine. The yields for these products are in the region of 60 to 80%, the best results generally being for the β-alanine analogs and the worst results generally being for the serine analogs.

1.3: Preparation of the Medium:

A gelled medium comprising L-alanyl-9-(4-amino-styryl)acridine (hereinafter referred to as L-Ala-4-ASA) or L-alanyl-aminophenylacridine (hereinafter referred to as L-Ala-APA) is prepared as follows: 46.37 g of Columbia agar are added to 1 liter of distilled water and then autoclaved. This reaction medium is separated into two media of equivalent volume. Each of these media comprises, respectively: 0.3 g/l of L-Ala-4-ASA provided by means of the stock solution in DMSO, and 0.3 g/l of L-Ala-APA also provided by means of a stock solution in DMSO.

Microorganisms derived from the applicant's collection were seeded onto each of the media, by delimitation as three dials, using a suspension at 0.5 McFarland. The dishes were incubated at 37° C. for 24 hours. The colonies formed were examined visually after incubation for 24 hours. The color of these colonies was noted before and after addition of a drop of hydrochloric acid.

1.4: Results:

The results are given in table 1 below. In the absence of HCl, the two substrates give no spontaneous coloration. In the presence of a drop of HCl, the colonies that possess the L-alanine-aminopeptidase activity are gray-mauve to mauve in color. The colonies that do not possess this activity remain colorless. These substrates are therefore sensitive and specific. They can, in the case of a mixed Gram-positive and Gram-negative culture, make it possible to separate the two types of microorganisms.

TABLE 1

Visualization of the L-alanine-aminopeptidase activity of microorganisms by means of L-Ala-4-ASA or L-Ala-APA on gelled medium

| SPECIES (internal strain no.) | 0.3 g/l L-Ala-4-ASA without HCl | 0.3 g/l L-Ala-APA without HCl | 0.3 g/l L-ala-4-ASA with HCl | 0.3 g/l L-Ala-APA with HCl |
|---|---|---|---|---|
| *Escherichia coli* | colorless | colorless | gray-mauve | pale mauve |
| *Proteus mirabilis* | colorless | colorless | gray-mauve | very pale-pale mauve |
| *Klebsiella pneumoniae* | colorless | colorless | gray-mauve | mauve |
| *Enterobacter cloacae* | colorless | colorless | gray-mauve | mauve |
| *Citrobacter koseri* | colorless | colorless | gray-mauve | mauve |
| *Streptococcus agalactiae* | colorless | colorless | colorless | colorless |
| *Enterococcus faecalis* | colorless | colorless | colorless | colorless |
| *Staphylococcus aureus* | colorless | colorless | colorless | colorless |
| *Listeria innocua* | colorless | colorless | colorless | colorless |
| *Candida albicans* | colorless | colorless | colorless | Colorless |

EXAMPLE 2

Visualization of the L-alanine-amino-peptidase Activity of Microorganisms on Gelled Medium Using a Quaternized Substrate 2.1: Molecule Used:

The L-alanine-aminopeptidase activity of microorganisms on gelled medium is determined using L-alanyl-9-(4-aminophenyl)-10-allylacridinium chloride (quaternized substrate), hereinafter denoted L-Ala-4-AP-10-AA, of formula:

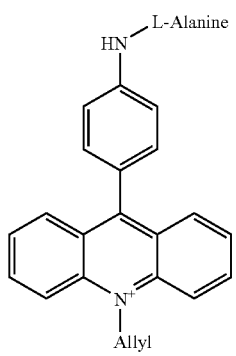

L-Alanyl-9-(4-aminophenyl)-10-allylacridinium Chloride 2.2: Synthesis of L-Ala-4-AP-10-AA:

The starting compound is t-Boc-alanyl-9-(4-amino-phenyl)acridine, the synthesis of which was already disclosed in paragraph 1.2.2 (Synthesis of L-Ala-APA). The t-Boc-alanyl-9-(4-aminophenyl)acridine (0.88 g, 2.0 mmol) is added to anhydrous tetrahydrofuran (4.0 ml), in a 10 ml flask that can be closed, and the mixture is heated to boiling so as to have a partial solution. The solution/suspension is cooled and allyl bromide (2.0 ml) is added. The flask is then refluxed for 8 hours, and the reaction is regularly monitored by thin layer chromatography (TLC). After cooling and elimination of the solvent, the quaternary salt is washed with diethyl ether and dried.

The product is dissolved in a minimum amount of ethanol and stirred with ethyl acetate (10 ml) saturated with HCl. Precipitates, that formed a few hours later, are recovered by filtration under reduced pressure. The introduction of ethyl ether into the filtrate makes it possible to recover the additional product. The combined fractions of the product are washed with ethyl ether and dried rapidly so as to prevent moisture absorption.

2.3: Preparation of the Medium:

A gelled medium comprising L-Ala-4-AP-10-AA as substrate is prepared as follows: 46.37 g of Columbia agar are added to 1 liter of distilled water and then autoclaved. The reaction medium is separated into three media of equivalent volume. Each of these media comprises, respectively, 0.1 g/l, 0.2 g/l, 0.4 g/l of L-Ala-4-AP-10-AA provided by means of a stock solution in DMSO.

Microorganisms derived from the applicant's collection were seeded onto each of the media, by delimitation as three dials, using a suspension at 0.5 McFarland. The dishes were incubated at 37° C. for 48 hours. The colonies formed were examined visually after incubation for 24 and 48 hours. The color of these colonies and also the intensity of this color were noted.

2.4: Results:

The results are expressed as color intensity, using an arbitrary scale range of from 0 to 4 as a basis. These results are given in table 2 below.

This substrate makes it possible to visualize L-alanine-aminopeptidase activity in Gram-negative bacteria through the spontaneous appearance (without the addition of acid) of a color concentrated in the colonies. The colonies that do not possess this activity remain colorless. This substrate is therefore sensitive and specific. It can make it possible, in the case of a mixed Gram-positive and Gram-negative culture, to separate the two types of microorganisms. "Quaternizing" the nitrogen in the 10-position of the acridine group makes it possible to obtain a spontaneous reaction without the addition of acid, compared to the same nonquaternized molecule described in example 1.

TABLE 2

Influence of the concentration of substrate in the visualization of the L-alanine-aminopeptidase activity of the microorganisms by means of that referred to as L-Ala-4-AP-10-AA

| STRAINS | Incubation time | 0.1 g/l of L-Ala-4-AP-10-AA | | 0.2 g/l of L-Ala-4-AP-10-AA | | 0.4 g/l of L-Ala-4-AP-10-AA | |
|---|---|---|---|---|---|---|---|
| | | Color | Intensity | Color | Intensity | Color | Intensity |
| Escherichia coli (032) | 24 H | beige | 0.5 | pink-orange | 2 | pink-orange | 2.5 |
| | 48 h | beige | 0.5 | pink-orange | 2 | pink-orange | 3 |
| Proteus mirabilis (103) | 24 H | beige | traces | pink-orange | 0.5 | pink-orange | 3 |
| | 48 h | beige | traces | pink-orange | 1 | pink-orange | 3 |
| Klebsiella pneumoniae (023) | 24 H | beige | traces | pink-orange | 1 | pink-orange | 3 |
| | 48 h | beige | traces | pink-orange | 2 | pink-orange | 3.5 |
| Citrobacter koseri (090) | 24 H | beige | 0.5 | pink-orange | 1 | pink-orange | 3 |
| | 48 h | beige | 0.5 | pink-orange | 2 | pink-orange | 3.5 |
| Staphylococcus aureus (070) | 24 H | inhibited | — | inhibited | — | inhibited | — |
| | 48 h | inhibited | — | inhibited | — | inhibited | — |
| Streptococcus pyogenes (067) | 24 H | inhibited | — | inhibited | — | inhibited | — |
| | 48 h | colorless | — | colorless | — | colorless | — |
| Enterococcus faecalis (075) | 24 H | colorless | — | orange | traces | orange | traces |
| | 48 h | colorless | — | orange | 0.5 | orange | 1 |
| Listeria innocua (036) | 24 H | colorless | — | colorless | — | colorless | — |
| | 48 h | colorless | — | colorless | — | colorless | — |
| Candida albicans (056) | 24 H | colorless | — | colorless | — | colorless | — |
| | 48 h | colorless | — | colorless | — | colorless | — |

EXAMPLE 3

Visualization of the L-alanine-amino-peptidase Activity of Microorganisms on Gelled Medium Using Another Quaternized Substrate 3.1: Molecule Used:

The visualization of the L-alanine-aminopeptidase activity of microorganisms on gelled medium is carried out using a substrate called L-alanyl-9-(4-amino-phenyl)-10-methylacridinium chloride (quaternized substrate), hereinafter called L-Ala-4-AP-10-MA, the formula of which is as below:

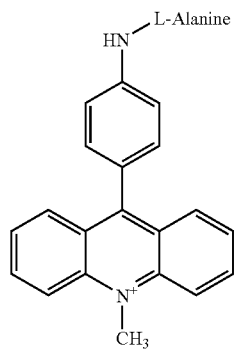

L-alanyl-9-(4-aminophenyl)-10-methylacridinium Chloride 3.2: Synthesis of L-Ala-4-AP-10-MA:

This synthesis was already carried out in paragraph 2.2 above, and in said synthesis, the allylbromide has been replaced with methyl iodide. Reference should be made thereto for the synthesis of L-Ala-4-AP-10-MA.

3.3: Preparation of the Medium:

A gelled medium comprising 300 mg/l of L-Ala-4-AP-10-MA is prepared as follows: 46.37 g of Columbia agar are added to 1 liter of distilled water and then autoclaved, and the substrate is then introduced by means of a stock solution in DMSO. Microorganisms derived from the applicant's collection were seeded onto the medium, by delimitation as three dials, using a suspension at 0.5 McFarland. The dishes were incubated at 37° C. for 48 hours. The colonies formed were examined visually after incubation for 24 and 48 hours. The color of these colonies and also the intensity of this color were noted.

3.4: Results:

The results are given in table 3 below:

TABLE 3

Visualization of the L-alanine-aminopeptidase activity of microorganisms by means of L-Ala-4-AP-10-AA for which the substrate concentration is optimized

| | | 0.3 g/l of L-Ala-4-AP-10-MA | |
|---|---|---|---|
| STRAINS | Incubation time | Color | Intensity |
| Escherichia coli (032) | 24 H | pink-orange | 3.5 |
| | 48 h | pink-orange | 3.5 |
| Proteus mirabilis (103) | 24 H | pink-orange | 1 |
| | 48 h | pink-orange | 2 |
| Klebsiella pneumoniae (023) | 24 H | pink-orange | 3 |
| | 48 h | pink-orange | 3 |
| Citrobacter koseri (090) | 24 H | pink-orange | 3 |
| | 48 h | pink-orange | 3 |
| Staphylococcus | 24 H | inhibited | — |

TABLE 3-continued

Visualization of the L-alanine-aminopeptidase activity of microorganisms by means of L-Ala-4-AP-10-AA for which the substrate concentration is optimized

| | | 0.3 g/l of L-Ala-4-AP-10-MA | |
|---|---|---|---|
| STRAINS | Incubation time | Color | Intensity |
| aureus (070) | 48 h | inhibited | — |
| Streptococcus pyogenes (067) | 24 H | inhibited | — |
| | 48 h | inhibited | — |
| Enterococcus faecalis (075) | 24 H | pink | traces |
| | 48 h | pink-orange | 0.5 |
| Listeria innocua (036) | 24 H | colorless | — |
| | 48 h | pink-orange | traces |
| Candida albicans (056) | 24 H | colorless | — |
| | 48 h | colorless | — |

This substrate makes it possible to visualize an L-alanine-aminopeptidase activity in Gram-negative bacteria by means of the spontaneous appearance (without the addition of acid) of a pink-orange color concentrated in the colonies. The colonies that do not have this activity remain colorless. This substrate is therefore sensitive and specific. It may make it possible, in the case of a Gram+/Gram− mixed culture, to separate the two types of microorganisms. Compared with the substrate described in example 2, it appears to make it possible to obtain greater color intensities for the positive strains. The difference between these two substrates is the type of group in the 10-position on the nitrogen of the acridine ring.

EXAMPLE 4

Visualization of the L-alanine-amino-peptidase Activity of Microorganisms on Gelled Medium Using Other Nonquaternized Substrates 4.1: Molecules Used The visualization of the L-alanine-aminopeptidase activity of microorganisms on gelled medium is carried out using two substrates called L-alanyl-2-methoxy-aminophenylacridine, hereinafter called L-Ala-2-MeOAPA, and L-alanyl-2,5-dimethoxyaminophenylacridine, hereinafter called L-Ala-2,5-diMeOAPA, the formulae of which are respectively as follows:

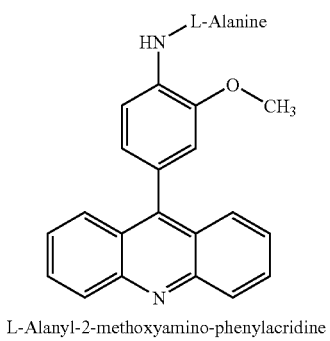

L-Alanyl-2-methoxyamino-phenylacridine

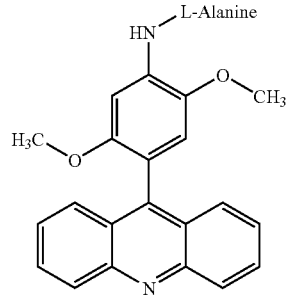

L-Alanyl-2,5-dimethoxyamino-phenylacridine 4.2: Synthesis of Substrates 4.2.1: Synthesis of L-Ala-2-MeOAPA On the basis of that which is described in point 1.2.2 above, other aniline analogs are also used to form novel products, including anisidine (3-methoxyaniline), which gives 9-(4-amino-2-methoxyphenyl)acridine.

4.2.2: Synthesis of L-Ala-2,5-diMeOAPA On the basis of that which is described in point 1.2.2 above, other aniline analogs are also used to form novel products, including 2,5-dimethoxyaniline, which gives 9-(4-amino-2,5-dimethoxyphenyl)acridine.

4.3: Preparation of the Medium:

A gelled medium comprising L-Ala-2-MeOAPA or L-Ala-2,5-diMeOAPA is prepared as follows: 46.37 g of Columbia agar are added to 1 liter of distilled water and then autoclaved. This reaction medium is separated into two media of equivalent volume. Each of these media comprises, respectively: 0.3 g/l of L-Ala-2-MeOAPA, introduced by means of a stock solution in DMSO, and 0.3 g/l of L-Ala-2,5-diMeOAPA, also introduced by means of a stock solution in DMSO. Microorganisms derived from the applicant's collection were seeded onto each of the media, by delimitation as three dials, using a suspension at 0.5 McFarland. The dishes were incubated at 37° C. for 24 hours. The color of these colonies and also the intensity of this color were noted after the addition of HCl.

4.4: Results

The results are given in table 4 below:

TABLE 4

Visualization of the L-alanine-aminopeptidase activity of microorganisms by means of L-Ala-2-MeOAPA and L-Ala-2,5-diMeOAPA

| | Incubation | L-Ala-2-MeOAPA | | L-Ala-2,5-diMeOAPA | |
|---|---|---|---|---|---|
| STRAINS | time | Color | Intensity | Color | Intensity |
| Escherichia coli (032) | 24 H | orange | 0.5 | Yellow-orange | 1.5 |
| | 48 h | pink | 3.5 | Yellow-orange | 2 |
| Proteus mirabilis (037) | 24 H | orange | 1 | colorless | 0 |
| | 48 h | orange | 1.5 | orange | 0.5 |
| Klebsiella pneumoniae (023) | 24 H | pink | 3 | orange | 1 |
| | 48 h | pink | 3.5 | Yellow-orange | 2.5 |
| Citrobacter koseri (012) | 24 H | orange | 2 | orange | 1 |
| | 48 h | pink | 3.5 | Yellow-orange | 2.5 |
| Enterobacter cloacae (061) | 24 H | pink | 2 | Yellow-orange | 1.5 |
| | 48 h | pink | 2 | Yellow-orange | 2 |
| Staphylococcus aureus (035) | 24 H | colorless* | 0 | colorless | 0 |
| | 48 h | colorless* | 0 | colorless | 0 |
| Streptococcus | 24 H | inhibited | — | colorless | 0 |

TABLE 4-continued

Visualization of the L-alanine-aminopeptidase
activity of microorganisms by means of L-Ala-2-MeOAPA
and L-Ala-2,5-diMeOAPA

| STRAINS | Incubation time | L-Ala-2-MeOAPA Color | Intensity | L-Ala-2,5-diMeOAPA Color | Intensity |
|---|---|---|---|---|---|
| agalactiae (001) | 48 h | inhibited | — | colorless | 0 |
| Enterococcus | 24 H | inhibited | — | Yellow-orange | 0.5 |
| faecalis (117) | 48 h | inhibited | — | Yellow-orange | 3 |
| Listeria innocua | 24 H | colorless* | 0 | colorless | 0 |
| (036) | 48 h | colorless* | 0 | colorless | 0 |
| Candida albicans | 24 H | inhibited | — | colorless | 0 |
| (077) | 48 h | inhibited | — | colorless | 0 |

*very poor growth

These two substrates make it possible, after the addition of a drop of HCl, to visualize an L-alanine-aminopeptidase activity in Gram-positive bacteria. The addition of (methoxy-)substituents to the phenyl group makes it possible, in addition, to reduce the toxicity of the substrates, in particular with respect to Gram-positive bacteria. However, this gain in fertility occurs to the detriment of the specificity; specifically, Enterococcus faecalis exhibits an activity with L-Ala-2,5-diMeOAPA after incubation for 48 hours.

EXAMPLE 5

Visualization of the β-alanine-amino-peptidase Activity of Microorganisms on Gelled Medium Use of β-alanyl-9-(4-aminophenyl)-10-methylacridinium Chloride (Quaternized Substrate)

5.1: Molecule Used:

The visualization of the β-alanine-aminopeptidase activity of microorganisms on gelled medium is carried out using a substrate called β-alanyl-9-(4-aminophenyl)-10-methylacridinium chloride (quaternized substrate), hereinafter called β-Ala-4-AP-10-MA, the formula of which is as below:

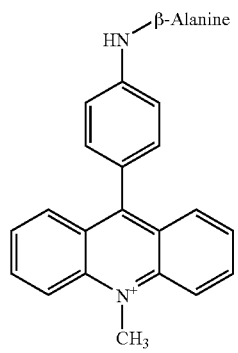

β-Alanyl-9-(4-aminophenyl)-10-methylacridinium Chloride 5.2: Synthesis of β-Ala-4-AP-10-MA:

The starting compound is t-Boc-alanyl-9-(4-amino-phenyl)acridine, the synthesis of which was already disclosed in paragraph 1.2.2 (Synthesis of L-Ala-APA). The t-Boc-alanyl-9-(4-aminophenyl)acridine (0.67 g, 1.5 mmol) is dissolved in acetonitrile (minimum volume) and refluxed with methyl iodide (4.0 ml). The flask is then closed and incubated at 40° C. for more than 100 hours. The solid reactant is dissolved as the reaction proceeds, forming an orange solution. Orangey-black crystals appear in this solution.

At the end of the 100 hours, the reaction mixture is transferred into ethyl acetate (100 ml) with stirring. After a required period of time, the quaternary salt is filtered and washed with diethyl ether.

The product is dissolved in a minimum amount of ethanol and stirred with ethyl acetate (10 ml) saturated with HCl. Precipitates, that are formed a few hours later, are recovered by filtration under reduced pressure. The introduction of diethyl ether into the filtrate makes it possible to recover further product. The combined fractions of the product are washed with diethyl ether and dried rapidly so as to prevent the absorption of moisture.

The deprotection is the same as that described above.

5.3: Preparation of the Medium:

A gelled medium comprising 300 mg/l of β-Ala-4-AP-10-MA is prepared as follows: 46.37 g of Columbia agar are added to 1 liter of distilled water and then autoclaved, and the substrate is then introduced by means of a stock solution in DMSO. Microorganisms derived from the applicant's collection were seeded onto the medium, by delimitation as three dials, using a suspension of 0.5 McFarland. The dishes were incubated at 37° C. for 48 hours. The colonies formed were examined visually after incubation for 24 and 48 hours. The color of these colonies and also the intensity of this color were noted.

5.4: Results:

The results are given in table 5 below.

This substrate makes it possible to visualize a β-alanine-aminopeptidase activity in Gram-negative bacteria by means of the spontaneous appearance (without the addition of acid) of an orange color concentrated in the colonies. The colonies that do not have this activity remain colorless. This substrate is therefore sensitive and specific. It makes it possible to identify Pseudomonas aeruginosa strains and in particular to differentiate them from other bacteria.

TABLE 5

Visualization of the β-alanine-aminopeptidase
activity of microorganisms by means of β-Ala-4-AP-10-MA

| STRAINS | Incubation time | 0.3 g/l of β-Ala-4-AP-10-MA Color | Intensity |
|---|---|---|---|
| Pseudomonas aeruginosa (052) | 24 H | orange | 2 |
| | 48 h | orange | 3 |
| Pseudomonas aeruginosa (165) | 24 H | orange | 1.5 |
| | 48 h | orange | 3 |
| Burkholderia cepacia (004) | 24 H | colorless | — |
| | 48 h | colorless | — |
| Pseudomonas fluorescens (016) | 24 H | inhibited | — |
| | 48 h | colorless | — |
| Pseudomonas stutzeri (073) | 24 H | inhibited | — |
| | 48 h | colorless | — |
| Pseudomonas putida (028) | 24 H | colorless | — |
| | 48 h | colorless | — |
| Acinetobacter calcoaceticus (034) | 24 H | colorless | — |
| | 48 h | colorless | — |
| Escherichia coli (032) | 24 H | colorless | — |
| | 48 h | colorless | — |
| Klebsiella pneumoniae (023) | 24 H | colorless | — |
| | 48 h | colorless | — |

EXAMPLE 6

Visualization of the L-proline-amino-peptidase Activity of Microorganisms on Gelled Medium Using a Proline-Based Nonquaternized Substrate 6.1: Molecule Used:

The visualization of the L-proline-aminopeptidase activity of microorganisms on gelled medium is carried out using a substrate called L-prolyl-9-(4-amino-phenyl)acridine (nonquaternized substrate), hereinafter called L-Pro-4-APA, the formula of which is as below:

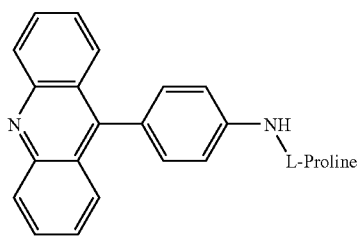

L-Prolyl-9-(4-aminophenyl)acridine 6.2: Synthesis of L-Pro-4-APA

This synthesis was already carried out in paragraph 1.2 above, according to two methods A and B, and in which methods the amino acid alanine has been replaced with the amino acid proline. Reference should be made thereto for the synthesis of L-Pro-4-APA.

6.3: Preparation of the Medium:

A gelled medium comprising L-prolyl-9-(4-amino-phenyl)acridine (hereinafter referred to as L-Pro-4-APA) is prepared as follows: 45 g of Sabouraud agar are added to 1 liter of distilled water and then autoclaved. This reaction medium comprises 0.3 g/l of L-Pro-APA also introduced by means of a stock solution in DMSO.

Microorganisms derived from the applicant's collection were seeded onto this medium, by delimitation as three dials, using a suspension of 0.5 McFarland. The dishes were incubated at 37° C. for 24 hours. The colonies formed were examined visually after incubation for 24 hours. The color of these colonies was noted before and after the addition of a drop of acetic acid, hereinafter referred to as GAA (glacial acetic acid).

6.4: Results:

The results are given in table 6 below:

TABLE 6

Visualization of the L-proline-aminopeptidase activity of microorganisms by means of L-Pro-4-APA for which the substrate concentration is optimized

| STRAINS | Drop of acetic acid | 0.3 g/l of L-Pro-4-APA | |
|---|---|---|---|
| | | Color | Intensity |
| Candida albicans (138) | before GAA | yellow | 2 |
| | after GAA | yellow | 3 |
| Candida parapsilosis (040) | before GAA | white | — |
| | after GAA | yellow | 2 |
| Candida lusitaniae (045) | before GAA | no growth | — |
| | after GAA | no growth | — |

TABLE 6-continued

Visualization of the L-proline-aminopeptidase activity of microorganisms by means of L-Pro-4-APA for which the substrate concentration is optimized

| STRAINS | Drop of acetic acid | 0.3 g/l of L-Pro-4-APA | |
|---|---|---|---|
| | | Color | Intensity |
| Candida guilliermondii (046) | before GAA | no growth | — |
| | after GAA | no growth | — |
| Candida krusei (026) | before GAA | yellow | 1 |
| | after GAA | yellow | 3 |
| Candida glabrata (051) | before GAA | yellow | 2 |
| | after GAA | yellow | 3 |

With certain *Candida* yeast strains, the inhibitory nature of the substrate is demonstrated. However, some yeasts produce a yellow color, without the addition of acid. This color is more intense for certain strains, in particular *Candida albicans*, and it is also more intense than in the absence of culture. This clearly demonstrates that our substrate, containing proline as amino acid, makes it possible to visualize L-proline-aminopeptidase activity in yeasts.

EXAMPLE 7

Visualization of the L-serine-aminopeptidase Activity of Microorganisms on Gelled Medium Using a Serine-Based Nonquaternized Substrate 7.1: Molecule Used:

The visualization of the L-serine-aminopeptidase activity of microorganisms on gelled medium is carried out using a substrate called L-seryl-9-(4-amino-phenyl)acridine (nonquaternized substrate), hereinafter called L-Ser-4-APA, the formula of which is as below:

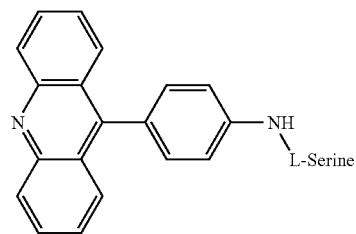

L-Seryl-9-(4-aminophenyl)acridine 7.2: Synthesis of L-Ser-4-APA:

Like that which was disclosed for L-Pro-4-APA (paragraph 6.2 above), this synthesis was already carried out in paragraph 1.2 above, according to two methods A and B, and in which methods the amino acid alanine has been replaced with the amino acid serine. Reference should be made thereto for the synthesis of L-Ser-4-APA.

7.3: Preparation of the Medium:

A gelled medium comprising L-seryl-9-(4-amino-phenyl)acridine (hereinafter referred to as L-Ser-4-APA) is prepared as follows: 30 milligrams of L-Ser-4-APA are added to 4 grams of Columbia agar, that are added to 0.1 liter of distilled water and then autoclaved. This reaction medium is autoclaved at 116° C. for 20 minutes. Most of the substrate is in solution, without residual coloration.

Microorganisms derived from the applicant's collection were seeded onto this medium using a suspension of 0.5 McFarland. The dishes were incubated at 37° C. for 24 hours. Samples of 10 µl of each suspension were cultured so as to produce colonies. The colonies formed were examined visually after incubation for 18 to 24 hours.

The color of these colonies was noted before and after the addition of a drop of acetic acid, hereinafter referred to as GAA (glacial acetic acid).

7.4: Results:

The results are given in table 7 below:

TABLE 7

Visualization of the L-serine-aminopeptidase activity of microorganisms by means of L-Ser-4-APA for which the substrate concentration is optimized

| STRAINS | GAA | 0.3 g/l of L-Ser-4-APA | |
| --- | --- | --- | --- |
| | | Color | Intensity |
| Escherichia coli (009) | before GAA | cream | — |
| | after GAA | pale orange | 2 |
| Klebsiella pneumoniae (012) | before GAA | cream | — |
| | after GAA | pale orange | 2 |
| Yersinia enterocolitica (061) | before GAA | cream | — |
| | after GAA | pale orange | 2 |
| Candida albicans (138) | before GAA | cream | — |
| | after GAA | cream | — |
| Staphylococcus aureus (008) | before GAA | cream | — |
| | after GAA | cream | — |
| Enterococcus faecalis (117) | before GAA | cream | — |
| | after GAA | cream | — |

Once again, there is a partial inhibition of certain strains with the acridine-based substrate. The three Gram-negative strains tested produce a particular reactional color after the addition of acetic acid.

EXAMPLE 8

Visualization of the L-alanine-amino-peptidase Activity of Microorganisms on Gelled Medium Using Quaternized Substrates Based on One, Two or Three L-alanines 8.1: Molecule Used:

The visualization of the L-alanine-aminopeptidase activity of microorganisms on gelled medium is carried out using three substrates, namely L-Ala-4-AP-10-MA as described in example 3, L-Ala-L-Ala-4-AP-10-MA which corresponds to L-Ala-4-AP-10-MA comprising an additional L-alanine, an L-Ala-L-Ala-L-Ala-4-AP-10-MA which has another additional L-alanine.

8.2: Synthesis of these Substrates:

These substrates were prepared as described in point 3.2 above, using the appropriate starting compound having one, two or three L-alanines.

8.3: Preparation of the Medium:

A gelled medium comprising these three substrates is prepared as follows: 30 mg of each substrate are dissolved (heating) in 10 ml of sterile distilled water. Ten ml of this solution are then added to 90 ml of Columbia agar kept molten at 50° C.

Various strains of microorganisms derived from the NCTC collection (National Collection of Type Cultures, Colindale, UK) were seeded onto the media thus obtained according to multipoint inoculation: for each strain, a drop of 10 µl of a suspension at 0.5 McFarland is deposited onto each of the culture media.

The colonies formed were examined visually after incubation for 24 h and 48 h. The color and the growth of these colonies were noted.

8.4: Results:

The results are given in table 8 below:

| STRAINS | L-Ala-4-AP-10-MA | | L-Ala-L-Ala-4-AP-10-MA | | L-Ala-L-Ala-L-Ala-4-AP-10-MA | |
| --- | --- | --- | --- | --- | --- | --- |
| (reference) | 24 h | 48 h | 24 h | 48 h | 24 h | 48 h |
| E. coli O157 (NCTC 12079) | Orange (++) | Orange (++) | Orange (++) | Orange (++) | Orange (++) | Orange (++) |
| Salmonella typhimurium (NCTC 74) | Orange (++) | Orange (++) | Orange (++) | Orange (++) | Orange (++) | Orange (++) |
| Salmonella poona (NCTC 4840) | Orange (++) | Orange (++) | Orange (++) | Orange (++) | Orange (++) | Orange (++) |
| Shigella sonnei (NCTC 9774) | Orange (++) | Orange (++) | Orange (++) | Orange (++) | Orange (++) | Orange (++) |
| Pseudomonas aeruginosa (NCTC 10662) | Orange (++) | Orange (++) | Orange (++) | Orange (++) | Orange (++) | Orange (++) |
| Klebsiella pneumoniae (NCTC 10896) | Orange (++) | Orange (++) | Orange (++) | Orange (++) | Orange (++) | Orange (++) |
| Enterobacter cloacae (NCTC 11936) | Orange (++) | Orange (++) | Orange (++) | Orange (++) | Orange (++) | Orange (++) |
| Burkholderia cepacia (NCTC 10743) | Orange (++) | Orange (++) | Orange (++) | Orange (++) | Orange (++) | Orange (++) |
| Serratia marcescens (NCTC 10211) | Orange (++) | Orange (++) | Orange (++) | Orange (++) | Orange (++) | Orange (++) |
| Enterococcus faecalis (NCTC 755) | NG | NG | Colorless (++) | Colorless (++) | Colorless (++) | Colorless (++) |
| Enterococcus faecalis (NCTC 12697) | Colorless (+/−) | Colorless (+/−) | Colorless (++) | Colorless (++) | Colorless (++) | Colorless (++) |
| Enterococcus faecium (NCTC 7171) | Colorless (++) | Colorless (++) | Colorless (++) | Colorless (++) | Colorless (++) | Colorless (++) |
| Listeria monocytogenes (NCTC 11994) | Colorless (++) | Colorless (++) | Colorless (++) | Colorless (++) | Colorless (++) | Colorless (++) |
| Staphylococcus aureus (NCTC 6571) | NG | NG | NG | NG | Colorless (++) | Colorless (++) |

-continued

| STRAINS (reference) | L-Ala-4-AP-10-MA | | L-Ala-L-Ala-4-AP-10-MA | | L-Ala-L-Ala-L-Ala-4-AP-10-MA | |
|---|---|---|---|---|---|---|
| | 24 h | 48 h | 24 h | 48 h | 24 h | 48 h |
| Staphylococcus aureus (NCTC 11939) | Colorless (++) | Colorless (++) | Colorless (++) | Colorless (++) | Colorless (++) | Colorless (++) |

++ means good growth,
+ means moderate growth,
+/− means poor growth and
NG means no growth On the three media, the Gram-negative bacterial strains formed orange-colored colonies, whereas the Gram-positive bacterial strains formed colorless colonies or did not develop. These three media therefore make it possible to differentiate Gram-negative bacteria from Gram-positive bacteria, and, according to the media, the growth of all or some of the strains tested.

EXAMPLE 9

Visualization of the pyroglutamine-amino-peptidase Activity of Microorganisms on Gelled Medium Using Quaternized Substrates Using pyroglutamyl-9-(4-aminophenyl)-10-methylacridine Hydrochloride Salt 9.1: Molecule Used:

The visualization of the pyroglutamine-aminopeptidase activity of microorganisms on gelled medium is carried out using pyroglutamyl-9-(4-aminophenyl)-10-methyl-acridine, hereinafter called PG-4-AP-10-MA.

9.2: Synthesis of this Substrate:

This substrate was prepared as described in point 3.2 above, except that the L-alanine was replaced with pyroglutamine.

9.3: Preparation of the Medium:

A gelled medium comprising this substrate is prepared as follows: 30 mg of each substrate are dissolved (heating) in 10 ml of sterile distilled water. Ten ml of this solution are then added to 90 ml of Columbia agar kept molten at 50° C.

Various strains of microorganisms derived from the NCTC collection (National Collection of Type Cultures, Colindale, UK) were seeded onto the media thus obtained according to the multipoint inoculation described in example 8 above.

The colonies formed were examined visually after incubation for 24 h and 48 h. The color and the growth of these colonies were noted.

9.4: Results:

The results are given in table 9 below:

| STRAINS (reference) | PG-4-AP-10-MA | |
|---|---|---|
| | 24 h | 48 h |
| Escherichia coli (NCTC 14018) | Colorless (++) | Colorless (++) |
| Escherichia coli 0157 (NCTC 12079) | Colorless (++) | Colorless (++) |
| Salmonella typhimurium (NCTC 74) | Colorless (++) | Colorless (++) |
| Salmonella Poona (NCTC 4840) | Colorless (++) | Colorless (++) |
| Shigella sonnei (NCTC 9774) | Colorless (++) | Colorless (++) |
| Pseudomonas aeruginosa (NCTC 10662) | Colorless (++) | Orange (++) |
| Klebsiella pneumonia (NCTC 10896) | Colorless (++) | Pale orange (++) |
| Enterobacter cloacae (NCTC 11936) | Colorless (++) | Pale orange (++) |
| Burkholderia cepacia (NCTC 10743) | Colorless (++) | Pale orange (++) |
| Serratia marcescens (NCTC 10211) | Colorless (++) | Pale orange (++) |

++ means good growth,
+ means moderate growth,
+/− means poor growth and NG means no growth The medium of the example makes it possible to differentiate bacteria that express pyroglutamyl-aminopeptidase activity from those that do not express it.

EXAMPLE 10

Visualization of the glycine-aminopeptidase Activity of Microorganisms on Gelled Medium Using a Quaternized Substrate Based on glycyl-9-(4-aminophenyl)-10-methylacridine Sydrochloride Salt 10.1: Molecule Used:

The visualization of the glycine-aminopeptidase activity of microorganisms on gelled medium is carried out using glycyl-9-(4-aminophenyl)-10-methylacridine, hereinafter called G-4-AP-10-MA.

10.2: Synthesis of this Substrate:

This substrate was prepared as described in point 3.2 above, except that the L-alanine was replaced with glycine.

10.3: Preparation of the Medium:

A gelled medium comprising this substrate is prepared as follows: 30 mg of the substrate are dissolved (heating) in 10 ml of sterile distilled water. Ten ml of this solution are then added to 90 ml of Columbia agar, kept molten at 50° C.

Various strains of microorganisms derived from the NCTC collection (National Collection of Type Cultures, Colindale, UK) were seeded onto the media thus obtained according to the multipoint inoculation described in example 8 above.

The colonies formed were examined visually after incubation for 24 h and 48 h. The color and the growth of these colonies were noted.

10.4: Results:

The results are given in table 10 below:

| STRAIN (reference) | G-4-AP-10-MA | |
|---|---|---|
| | 24 h | 48 h |
| *Escherichia coli* (NCTC 14018) | NG | NG |
| *Escherichia coli* O157 (NCTC 12079) | Orange (++) | Orange (++) |
| *Salmonella typhimurium* (NCTC 74) | Pale orange (++) | Pale orange (++) |
| *Salmonella poona* (NCTC 4840) | Orange (++) | Orange (++) |
| *Shigella sonnei* (NCTC 9774) | Orange (++) | Orange (++) |
| *Pseudomonas aeruginosa* (NCTC 10662) | Pale orange (++) | Orange (++) |
| *Klebsiella pneumonia* (NCTC 10896) | Orange (++) | Orange (++) |
| *Enterobacter cloacae* (NCTC 11936) | Orange (++) | Orange (++) |
| *Burkholderia cepacia* (NCTC 10743) | Orange (++) | Orange (++) |
| *Serratia marcescens* (NCTC 10211) | Orange (++) | Orange (++) |
| *Enterococcus faecalis* (NCTC 755) | NG | NG |
| *Enterococcus faecalis* (NCTC 12697) | Colorless (+) | Colorless (+) |
| *Enterococcus faecium* (NCTC 7171) | Colorless (+) | Colorless (+) |
| *Listeria monocytogenes* (NCTC 11994) | Colorless (+) | Colorless (+) |
| *Staphylococcus aureus* (NCTC 6571) | NG | NG |
| *Staphylococcus aureus* (NCTC 11939) | Colorless (+) | Colorless (+) |

++ means good growth,
+ means moderate growth,
+/− means poor growth and NG means no growth The medium of the example makes it possible to differentiate the bacteria that express glycylamyl-aminopeptidase activity from those that do not express it.

EXAMPLE 11

Visualization of the t-BOC-L-alanyl-L-alanyl-L-alanyl-peptidase Activity of Microorganisms on Gelled Medium Using a Quaternized Substrate for Which the Amino Acid is Coupled to a Blocking Agent, a Substrate Based on t-BOC-L-alanyl-L-alanyl-L-alanyl-9-(4-aminophenyl)-10-methylacridine Hydrochloride Salt 11.1: Molecule Used:

The visualization of the L-alanine-aminopeptidase activity of microorganisms on gelled medium is carried out using t-BOC-L-alanyl-L-alanyl-L-alanyl-9-(4-amino-phenyl)-10-methylacridine, hereinafter called t-BOC-L-Ala-4-AP-10-MA.

11.2: Synthesis of this Substrate:

This substrate was prepared as described in point 3.2 above, with the exception that the deprotection of the amino compound was not carried out.

11.3: Preparation of the Medium:

A gelled medium comprising this substrate is prepared as follows: 30 mg of the substrate are dissolved (heating) in 10 ml of sterile distilled water. Ten ml of this solution are then added to 90 ml of Columbia agar, kept molten at 50° C.

Various strains of microorganisms derived from the NCTC collection (National Collection of Type Cultures, Colindale, UK) were seeded onto the media thus obtained according to the multipoint inoculation described in example 8 above.

The colonies formed were examined visually after incubation for 24 h and 48 h. The color and the growth of these colonies were noted.

11.4: Results:

The results are given in table 11 below:

| STRAIN (reference) | t-BOC-L-Ala-Ala-Ala-4-AP-10-MA | |
|---|---|---|
| | 24 h | 48 h |
| *Escherichia coli* O157 (NCTC 12079) | Pale orange (++) | Pale orange (++) |
| *Salmonella typhimurium* (NCTC 74) | Pale orange (++) | Pale orange (++) |
| *Salmonella poona* (NCTC 4840) | Pale orange (++) | Pale orange (++) |
| *Shigella sonnei* (NCTC 9774) | Pale orange (++) | Pale orange (++) |
| *Pseudomonas aeruginosa* (NCTC 10662) | Pale orange (++) | Pale Orange (++) |
| *Klebsiella pneumonia* (NCTC 10896) | Orange (++) | Orange (++) |
| *Enterobacter cloacae* (NCTC 11936) | Orange (++) | Orange (++) |
| *Burkholderia cepacia* (NCTC 10743) | Orange (++) | Orange (++) |
| *Serratia marcescens* (NCTC 10211) | Orange (++) | Orange (++) |
| *Enterococcus faecalis* (NCTC 755) | NG | NG |
| *Enterococcus faecalis* (NCTC 12697) | Colorless (+/−) | Colorless (+/−) |
| *Enterococcus faecium* (NCTC 7171) | Colorless (+/−) | Colorless (++) |
| *Listeria monocytogenes* (NCTC 11994) | Colorless (+/−) | Colorless (+) |
| *Staphylococcus aureus* (NCTC 6571) | NG | NG |
| *Staphylococcus aureus* (NCTC 11939) | Colorless (+) | Colorless (+) |

++ means good growth,
+ means moderate growth,
+/− means poor growth and NG means no growth The medium of the example makes it possible to obtain four groups of microorganisms:
- those that form true orange-colored colonies,
- those that form pale orange-colored colonies,
- those that form colorless colonies, and
- those that do not form colonies.

Among the strains tested, the Gram-negative bacteria belong to the first two groups, whereas the Gram-positive bacteria belong to the last two.

The presence of a blocking agent (t-Boc) makes it possible to modulate the activity compared with the results obtained with the deprotected substrate (see example 8 above).

Other Experiments Carried Out:

Other substrates were tested, that make it possible to validate the results presented here; mention may, for example, be made of:
- L-alanyl-9-(4-amino-3-methoxyphenyl)-10-methyl-acridinium chloride,
- L-alanyl-9-(4-aminophenyl)-10-methylacridinium chloride hydrochloride,
- L-alanyl-9-(4-amino-2,5-dimethoxyphenyl)-10-methyl-acridinium chloride hydrochloride,
- β-alanyl-9-(4-aminophenyl)-10-methylacridinium chloride hydrochloride,
- β-alanyl-9-(4-amino-2-methoxyaminophenyl)acridine,
- β-alanyl-9-(4-amino-2,5-dimethoxyamino-phenyl)acridine,
- β-alanyl-9-(4-amino-3-methoxyphenyl)-10-methyl-acridinium chloride hydrochloride,
- β-alanyl-9-(4-amino-2,5-dimethoxyphenyl)-10-methyl-acridinium chloride hydrochloride.

Similarly, other species of microorganisms, generally bacteria, were also tested, such as:
*Salmonella typhimurium,*
*Staphylococcus epidermidis*
*Serratia marcescens.*

The invention claimed is:

1. A chromogenic enzyme substrate with the formula (I) below:

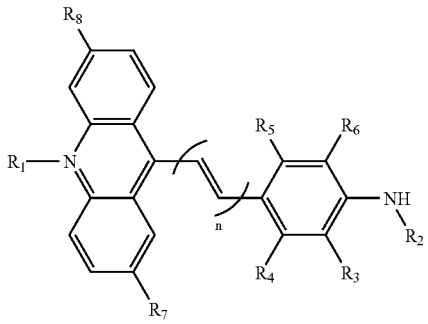

(I)

wherein:
- $R_1$ is nothing or an alkyl, allyl or aryl group;
- $R_2$ is at least one amino acid;
- $R_3$, $R_4$, $R_5$ and $R_6$ are, independently of one another, H— or O-alkyl;
- $R_7$ is H, O—$CH_3$, alkyl or halogen;
- $R_8$ is H or Cl; and
- n is an integer corresponding to 0 or 1.

2. The substrate as claimed in claim 1, wherein $R_2$ is coupled to a blocking agent.

3. The substrate as claimed in claim 1, wherein $R_1$ is a methyl or allyl group.

4. The substrate as claimed in claim 1, wherein $R_2$ is alanine.

5. The substrate as claimed in claim 1, wherein $R_3$, $R_4$, $R_5$ and $R_6$, are independently of one another, O-$CH_3$.

6. The substrate as claimed in claim 1, having the formula (Ia) below:

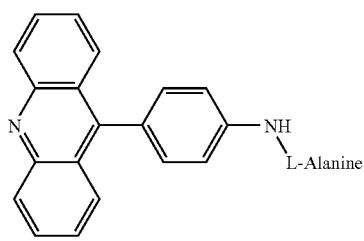

(Ia)

or formula (Ib) below:

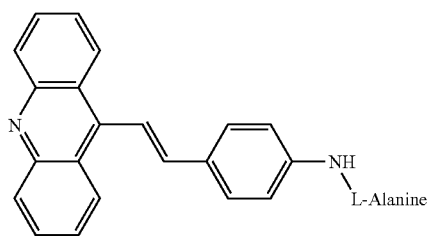

(Ib)

7. The substrate as claimed in claim 6, wherein the L-alanine is coupled to a blocking agent.

8. The substrate as claimed in claim 1, having the formula (Ic) below:

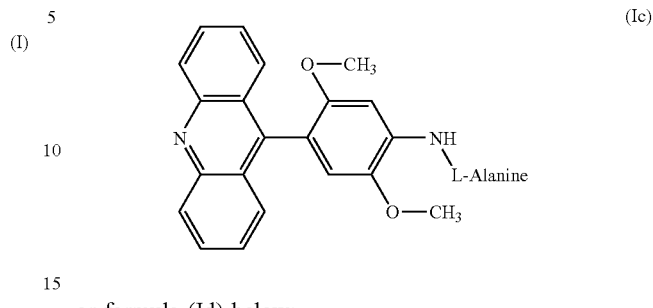

(Ic)

or formula (Id) below:

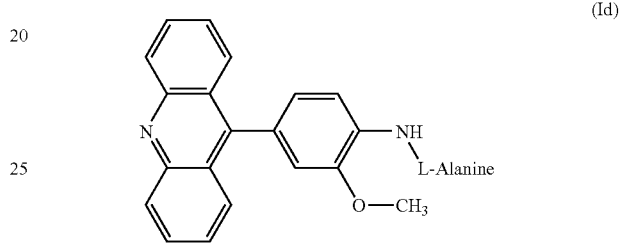

(Id)

9. The substrate as claimed in claim 8, wherein the L-alanine is coupled to a blocking agent.

10. A culture medium comprising at least one chromogenic enzyme substrate as claimed in claim 1.

11. The medium as claimed in claim 10, wherein the medium is a gelled medium.

12. A method detecting Gram Negative bacteria, comprising:
a) providing a culture medium as claimed in claim 10;
b) seeding the culture medium with a biological sample to be tested;
c) incubating the seeded culture medium; and
d) visualizing the presence of at least one color synonymous with the presence of at least one bacterium of the Gram-negative type.

13. A method for detecting at least one aminopeptidase activity in microorganisms, comprising:
a) providing a culture medium as claimed in claim 10;
b) seeding the culture medium with a biological sample to be tested;
c) incubating the seeded culture medium; and
d) visualizing the presence of at least one aminopeptidase activity.

14. The method as claimed in claim 13, wherein when the nitrogen in the 10-position of the acridine group is not quaternized, the presence of at least one aminopeptidase activity is visualized by adding an acid to the culture medium.

15. The method as claimed in claim 14, wherein the acid is hydrochloric acid, acetic acid or citric acid.

16. The culture medium as claimed in claim 10, further comprising at least one other enzyme substrate specific for an enzyme activity different from an aminopeptidase activity.

17. A method for detecting at least one aminopeptidase activity and at least one enzyme activity different from an aminopeptidase activity in Gram-negative bacteria, comprising:
  a) providing a culture medium as claimed in claim 16;
  b) seeding the culture medium with a biological sample to be tested;
  c) incubating the seeded culture medium;
  d) visualizing the presence of at least one aminopeptidase activity; and
  e) visualizing the presence of at least one enzyme activity different from an aminopeptidase activity.

* * * * *